US009291609B2

United States Patent
Earl et al.

(10) Patent No.: US 9,291,609 B2
(45) Date of Patent: Mar. 22, 2016

(54) SENSOR SYSTEM FOR FUEL TRANSPORT VEHICLE

(71) Applicant: UT-Battelle, LLC, Oak Ridge, TN (US)

(72) Inventors: Dennis Duncan Earl, Knoxville, TN (US); Timothy J. McIntyre, Farragut, TN (US); David L. West, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 376 days.

(21) Appl. No.: 13/787,430

(22) Filed: Mar. 6, 2013

(65) Prior Publication Data

US 2013/0283893 A1  Oct. 31, 2013

Related U.S. Application Data

(60) Provisional application No. 61/640,356, filed on Apr. 30, 2012.

(51) Int. Cl.
*G01N 33/22* (2006.01)
*C10L 1/00* (2006.01)
*G01N 33/28* (2006.01)

(52) U.S. Cl.
CPC ............... *G01N 33/22* (2013.01); *C10L 1/003* (2013.01); *G01N 33/2882* (2013.01)

(58) Field of Classification Search
CPC ..... C10L 1/003; G01N 33/22; G01N 33/2882
USPC ........... 73/61.71; 141/29, 83, 96, 98
See application file for complete search history.

(56) References Cited

U.S. PATENT DOCUMENTS

| 4,815,436 | A | 3/1989 | Sasaki et al. |
| 5,525,516 | A | 6/1996 | Krutak et al. |
| 5,878,772 | A | 3/1999 | Belyea |
| 5,928,954 | A * | 7/1999 | Rutledge et al. ............... 436/56 |
| 6,234,557 | B1 | 5/2001 | Bae |
| 6,871,677 | B2 * | 3/2005 | Zerangue, Sr. ............... 141/83 |
| 6,881,381 | B1 * | 4/2005 | Asher et al. ............... 422/68.1 |

(Continued)

FOREIGN PATENT DOCUMENTS

| CA | 990716 A1 | 6/1976 |
| CA | 2498468 | * 8/2006 |

(Continued)

OTHER PUBLICATIONS

Marion et al., "Fuel Tax Incidence, Supply Conditions and Tax Evasion," 41 pages (2009).

*Primary Examiner* — Daniel S Larkin
(74) *Attorney, Agent, or Firm* — Klarquist Sparkman, LLP

(57) ABSTRACT

An exemplary sensor system for a fuel transport vehicle can comprise a fuel marker sensor positioned between a fuel storage chamber of the vehicle and an access valve for the fuel storage chamber of the vehicle. The fuel marker sensor can be configured to measure one or more characteristics of one or more fuel markers present in the fuel adjacent the sensor, such as when the marked fuel is unloaded at a retail station. The one or more characteristics can comprise concentration and/or identity of the one or more fuel markers in the fuel. Based on the measured characteristics of the one or more fuel markers, the sensor system can identify the fuel and/or can determine whether the fuel has been adulterated after the marked fuel was last measured, such as when the marked fuel was loaded into the vehicle.

19 Claims, 11 Drawing Sheets

(56) References Cited

U.S. PATENT DOCUMENTS

| | | | |
|---|---|---|---|
| 7,227,139 B2* | 6/2007 | Kram et al. | 250/301 |
| 7,885,428 B2* | 2/2011 | Stierman et al. | 382/100 |
| 8,825,361 B1* | 9/2014 | Bernhardt | 701/123 |
| 8,905,089 B2* | 12/2014 | Evans | 141/231 |
| 2004/0248307 A1 | 12/2004 | Grof et al. | |
| 2008/0184775 A1 | 8/2008 | Yamagishi et al. | |
| 2009/0216419 A1 | 8/2009 | Shaw | |
| 2010/0089486 A1* | 4/2010 | Koeninger et al. | 141/2 |
| 2010/0208260 A1* | 8/2010 | Carr et al. | 356/326 |

FOREIGN PATENT DOCUMENTS

| | | | |
|---|---|---|---|
| JP | 6-144499 | * | 5/1994 |
| WO | WO 00/02034 | * | 1/2000 |
| WO | WO 2008/084815 A1 | | 7/2008 |
| WO | WO 2010/004352 | * | 1/2010 |

* cited by examiner

SENSOR SYSTEM FOR FUEL TRANSPORT VEHICLE

CROSS REFERENCE TO RELATED APPLICATION

This application claims the benefit of U.S. Provisional Application No. 61/640,356 filed on Apr. 30, 2012, and entitled "SENSOR SYSTEM FOR FUEL TRANSPORT VEHICLE," which is hereby incorporated herein by reference in its entirety.

STATEMENT REGARDING FEDERALLY SPONSORED RESEARCH OR DEVELOPMENT

This invention was made with government support under Contract No. DE-AC05-00OR22725 awarded by the U.S. Department of Energy. The government has certain rights in the invention.

FIELD

This disclosure is related to sensor systems for a fuel transport vehicle.

BACKGROUND

Diesel fuel for over-road use is taxed at a higher level (the "fuel tax") than off-road use petroleum products such as agricultural/marine diesel and heating oil. These latter products are typically marked with dyes to distinguish them from over-road diesel fuel. The typical method to detect use of dyed products for over-road use is visual inspection, which can only be applied to a small fraction of the fuel sold for, and used in, over-road transportation. There also exist numerous methods to evade paying the fuel tax, and it is often suspected that fuel purchased in a state with a particular fuel tax is actually meant for use in a nearby higher-tax state. These schemes and this misdirection of fuel can often only be detected in hindsight and can be difficult to prove, leading to significant losses of revenue.

SUMMARY

Disclosed sensors and sensor systems can determine the identity of a fuel within a fuel transport vehicle and can detect changes to the fuel occurring while the fuel is within the fuel transport vehicle.

In some embodiments, a sensor system for a fuel transport vehicle comprises a fuel marker sensor positioned between a fuel storage chamber of the vehicle and an access valve for the fuel storage chamber of the vehicle. The fuel marker sensor can be configured to measure one or more characteristics of one or more fuel markers present in the fuel as the fuel flows past the fuel marker sensor, such as when the marked fuel is unloaded at a retail station. The one or more characteristics can comprise concentration and/or identity of the one or more fuel markers in the fuel. Based on the measured characteristics of the one or more fuel markers, the sensor system can identify the fuel and/or can determine if the fuel has been adulterated after the marked fuel was last measured, such as when the marked fuel was loaded into the vehicle. This measurement can be done in real time as the fuel is being unloaded, rather than needing to take a sample of the fuel to a remote laboratory for testing at a later time. Measuring the marked fuel in real time can determine whether tax fraud and/or adulteration of the fuel has occurred before the unloading operation is complete, such that the operation can be stopped or preempted if certain characteristics are detected by the system.

Some embodiments of a fuel marker sensor can comprise a first light source configured to emit light in a first spectral range, a second light source configured to emit light in a second spectral range, and a lens having spherical aberration and configured to direct light from the first and second light sources to a region or volume of a marked fuel. The light from the first light source can cause the fuel to emit fluorescence in a third spectral range and the light from the second light source can cause the at least one marker to emit fluorescence in a fourth spectral range. The sensor can further comprise a first light detector, a second light detector, a first filter positioned over the first light detector, and a second filter positioned over the second light detector. The lens can be configured to direct the fluorescence from the fuel and the marker toward the filters and the light detectors. The first filter can be configured to transmit the fluorescence from the fuel to the first light detector and to block the fluorescence from the at least one marker. The second filter can be configured to transmit the fluorescence from the at least one marker to the second light detector and to block the fluorescence from the fuel.

An exemplary method of measuring a fuel marker comprises: positioning a fuel marker sensor between a fuel storage chamber of a fuel transport vehicle and an access valve for the fuel storage chamber; and using the fuel marker sensor to measure the concentration of a fuel marker present in fuel as the fuel flows out of the fuel storage chamber toward the access valve. In some methods, a fuel transport vehicle is retrofitted with a fuel marker sensor by replacing an existing sight glass spacer on the vehicle with a spacer designed to accommodate the fuel marker sensor.

The foregoing and other objects, features, and advantages of the disclosure will become more apparent from the following detailed description, which proceeds with reference to the accompanying figures.

DETAILED DESCRIPTION

Figure 1:
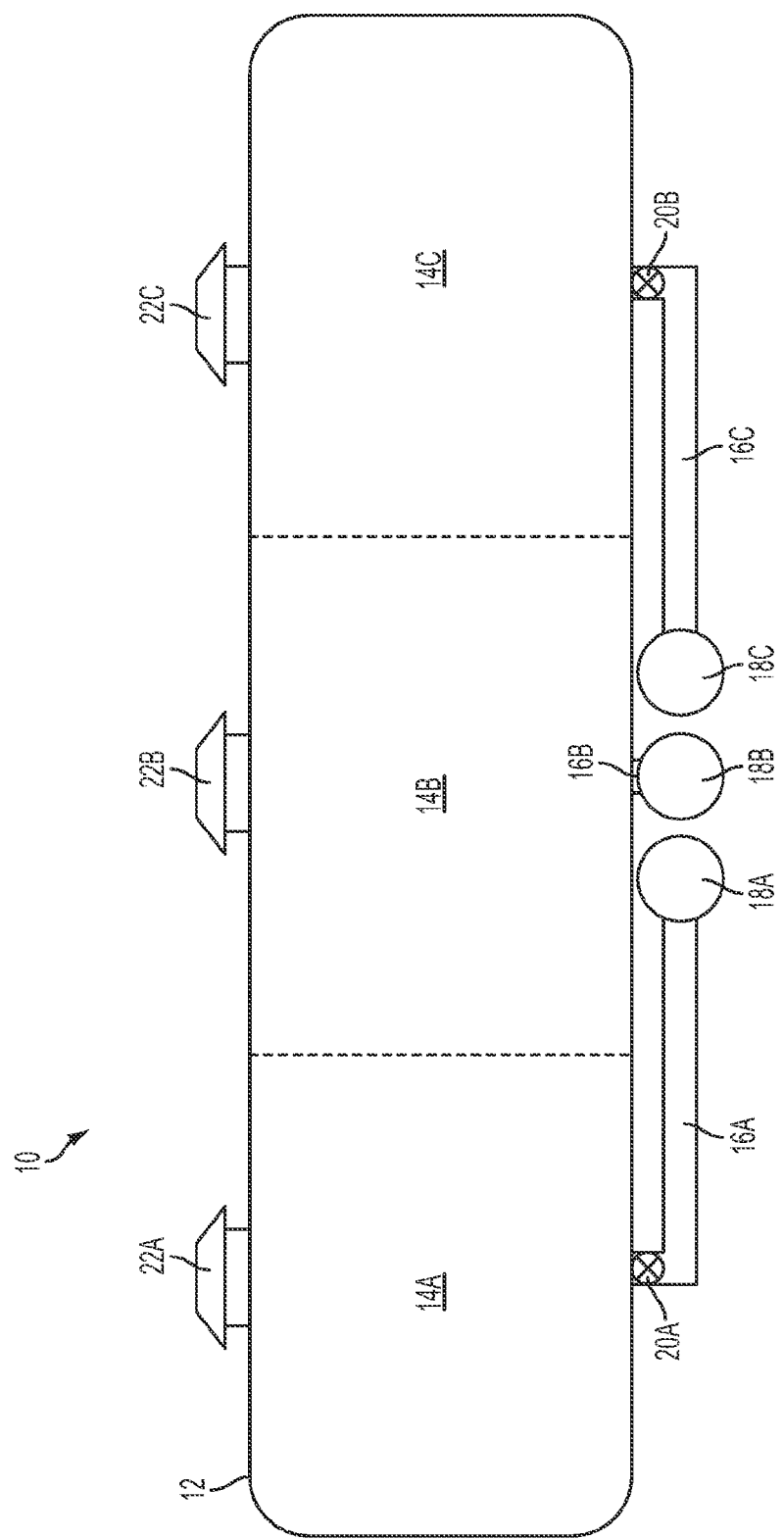
FIG. 1 illustrates an exemplary fuel transport vehicle.

FIG. 1 shows an exemplary fuel transport vehicle 10. The vehicle 10 can comprise a trailer having a fuel storage container, or tank, 12 that is divided in several compartments, or chambers, 14. In FIG. 1, three compartments 14A, 14B, and 14C are shown. Each compartment 14 can have a corresponding lower conduit 16 and an access valve, or fill valve, 24 (FIG. 3) coupled to the lower end of each conduit 16. The access valves 24 can comprise an inlet/outlet port 18 for adding and removing fuel to or from the particular compartment 14 when the access valve 24 is opened. The access valve 24 can comprise a handle 26 for manually opening and closing the port 18. Each conduit 16 can comprise an emergency valve 20 adjacent the compartment 14 to prevent uncontrolled release of the compartment contents should the plumbing and valves below it become compromised. Each compartment 14 can also have an upper hatch 22.

Filling and emptying the compartments 14 is typically done through the access valves 24 and the conduits 16. In one example, fuel can be pumped into the compartment 14 at about 500 gallons per minute, while emptying the fuel from the compartment is generally done via gravity, so the flow rate can vary continuously throughout an off-load operation depending on the current fuel level within the compartment.

Figure 2:
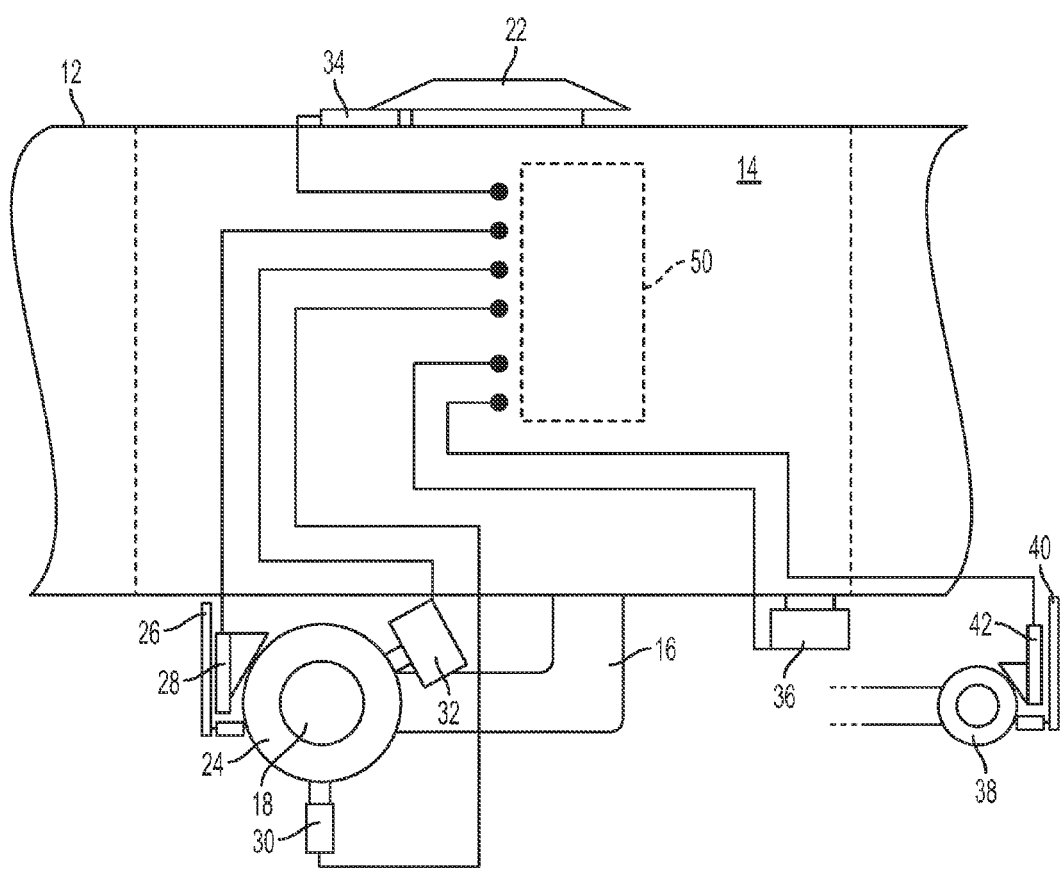
FIG. 2 illustrates an exemplary sensing system for the fuel transport vehicle of FIG. 1.

In typical fuel transport trailers, the access valve 24 and the hatch 22 are the only two access points for each compartment 14. The compartments may also have a vapor recovery conduit and valve 38 (FIG. 2). In addition, each compartment 14 is typically isolated and has its own independent fuel level and the fuel in each compartment can be different from the fuel in the other compartments.

The disclosed sensor system can have several functions that are useful in evaluating whether or not fuel tax evasion is occurring or has occurred with regard to the fuel in the vehicle 10. One exemplary function of the sensor system can be to determine if any of the access points into a particular compartment 14 are currently open or have been opened during a certain time period. Another exemplary function of the sensor system can be to determine how much fuel is present in each of the compartments 14, which can be a function of the fuel level in the compartment. Yet another exemplary function of the sensor system can be to determine the identity of the fuel in each compartment and/or determine if the fuel has been changed or adulterated during a certain time period, such as between the time when fuel taxes were paid at a load point and the time when the fuel is unloaded at a retail station. In some embodiments, the sensor system is capable of performing at least each of these functions.

To determine if any of the access points into the trailer 10 or a particular compartment 14 are currently open or have been opened during a certain time period, the sensor system can be capable of monitoring the access valve 24, the hatch 22, and optionally the vapor recovery valve 38 for each compartment 14. The sensor system can determine whether or not each of these access points are closed at any given time, and output a binary result that indicates either "closed" or "not closed." If any of the access points are determined to be not closed at a time between a load point and a unload point, that can indicate the fuel may have been adulterated. For example, if an access point is determined to have been opened at an unexpected time, such as between planned unloading events, this can be evidence that someone may have added another substance to the fuel and/or that tax evasion has occurred. Further, if it is later determined that the fuel was adulterated at some point during a certain time frame, one can then look into the times when it was determined that the access points were opened to determine how and when the fuel was adulterated.

To determine how much fuel is present in each of the compartments 14, the sensor system can comprise a fuel level sensor for each compartment. If the fuel level in a given compartment 14 has increased between a load point and an unload point, that can indicate that additional fuel or another substance has been added to the compartment, and if the fuel level has decreased, that can indicate that some of the fuel has been removed and possibly other substances have been added. Such addition or removal can be evidence that tax evasion has occurred, especially if the addition or removal occurred at an unexpected time.

To determine the identity of the fuel in each compartment, the sensor system can comprise a means for determining the concentration of a fuel marker in the fuel while the fuel is within a fuel transport vehicle. For example, the sensor system can comprise a fuel marker sensor 32 for each compartment that is capable of detecting one or more markers present in the fuel that identify the fuel. A specific marker or combination of markers can be added to a fuel prior to, or after, loading the fuel into the vehicle 10. When the fuel is unloaded, the fuel marker sensor can detect the presence and concentration of the marker(s). If the unloaded fuel comprises different markers or a different concentration of the markers compared to the fuel that was loaded into the trailer, that can indicate that the fuel has been adulterated.

FIG. 2 illustrates an exemplary embodiment of a sensor system for a fuel transport vehicle. The sensor system can comprise an access valve sensor 28, a hatch sensor 34, a fuel level sensor 30, a fuel marker sensor 32, a vapor recovery valve sensor 42, one or more trailer sensors 36, and/or additional sensors. The various sensors can be electrically coupled to a central controller 50.

The access valve sensor 28, hatch sensor 34, and vapor recover valve sensor 42 can comprise position sensors, or proximity sensors, that can detect the position of, or proximity of, a certain object. These sensors can comprise magnetic proximity switches that close when a target magnet is moved within a certain proximity of a sensing face of the sensor.

Figure 4A:
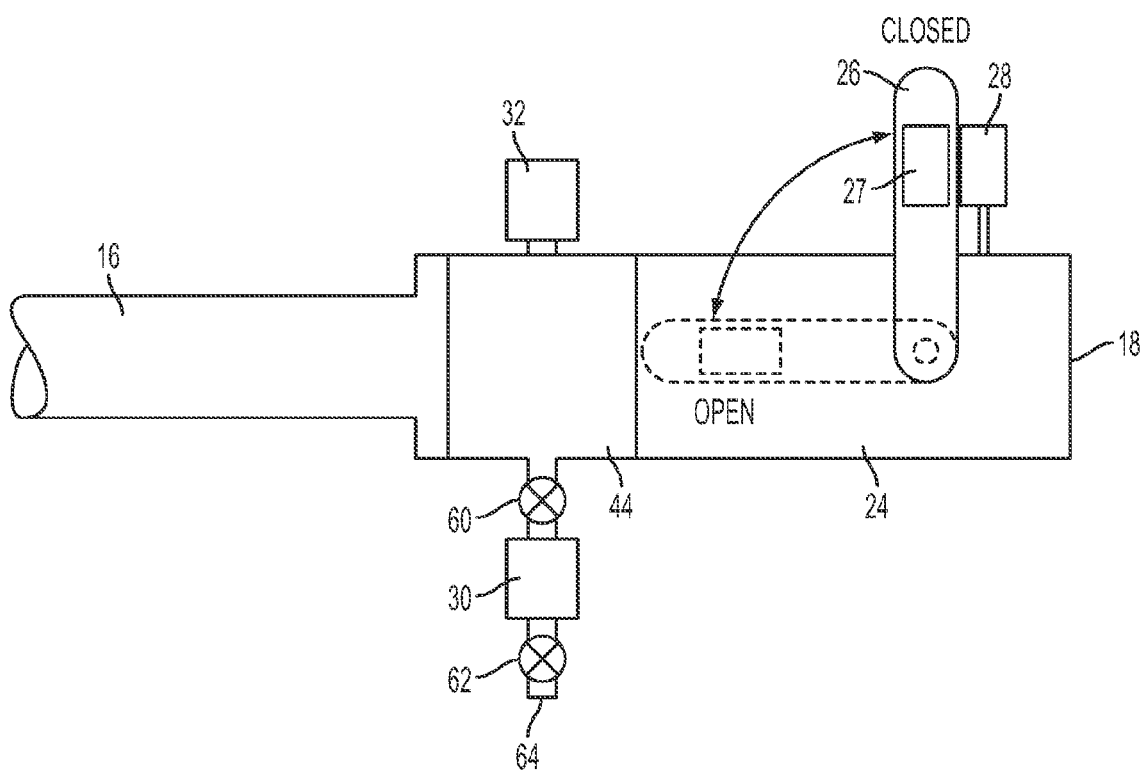
FIG. 4A is a schematic view of an exemplary port for a fuel transport vehicle.
Figure 4B:
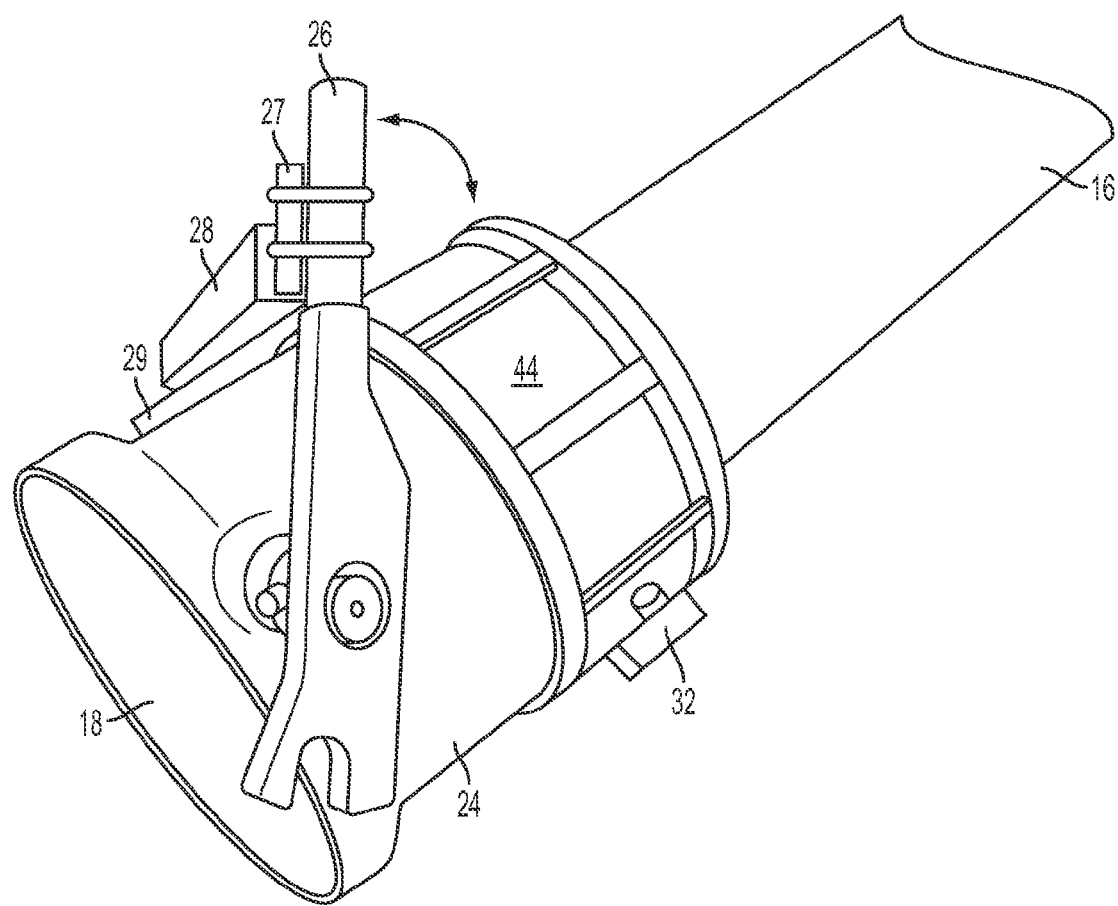
FIG. 4B is a perspective view of an exemplary port for a fuel transport vehicle.

As shown in FIGS. 2, 4A and 4B, the access valve sensor 28 can be coupled to the access valve 24 adjacent to the access valve handle 26. A target magnet 27 can be coupled to the handle 26 (as shown in FIGS. 4A and 4B) since the handle 26 is typically made of aluminum. The sensor 28 can be mounted such that when the handle 26 is in the closed position (i.e., the access valve 24 is closed) the target magnet 27 is positioned adjacent to the sensor 28, thereby closing the proximity switch of the sensor 28 and causing the sensor 28 to indicate that the access valve 24 is closed. When the handle 26 is rotated to open the access valve 24, the target 27 is moved away from the sensor 28, causing the sensor 28 to indicate that the access valve is not closed. The sensor 28 can be mounted to the access valve 24 via a plate 29 (as shown in FIG. 4B), for example.

The vapor recovery valve sensor 42 can be similar to the access valve sensor 28. The sensor 42 can be mounted on the vapor recovery valve 38 adjacent to its handle 40 such that the handle is adjacent a sensing face of the sensor 42 when the handle 40 is in the closed position. A magnetic target can be coupled to the handle 40. If the handle 40 is rotated from the closed position, the target moves away from the sensor 42 causing the sensor 42 to indicate that the vapor recovery valve 38 is not closed.

The hatch sensor 34 can also be similar to the access valve sensor 28. The hatch sensor 34 can be mounted on the top of the compartment 14 adjacent to its hatch 22 such that a portion of the hatch is adjacent a sensing face of the sensor 34 when the hatch is in the closed position, as shown in FIG. 2. A magnetic target can be coupled to the hatch 22. If the hatch 22 is pivoted open, or otherwise moved from the closed position, the magnetic target moves away from the hatch sensor 34 causing the hatch sensor to indicate that the hatch 22 is not closed.

The fuel level sensor 30 can comprise a pressure-based sensor. The fuel sensor 30 can be coupled to the access valve 24, the conduit 16, an insert 44, or any other point below the level of the bottom of the compartment 14. The fuel sensor can be configured to be in fluid contact with the fuel, such as during unloading and loading of the fuel through the access valve 24 and conduit 16. The fuel sensor can measure the fluid pressure of the fuel, which can be used to calculate the fuel level within the compartment 14, such as by the controller 50, based on a known density of the fuel in the compartment. The fuel level (distance from the pressure measurement point to the top of the fuel in the compartment) can be proportional to the measured pressure divided by the density of the fuel. For example, the fluid pressure can be equal to the product of fuel height, the density of the fuel, and the gravitational constant.

Figure 3:
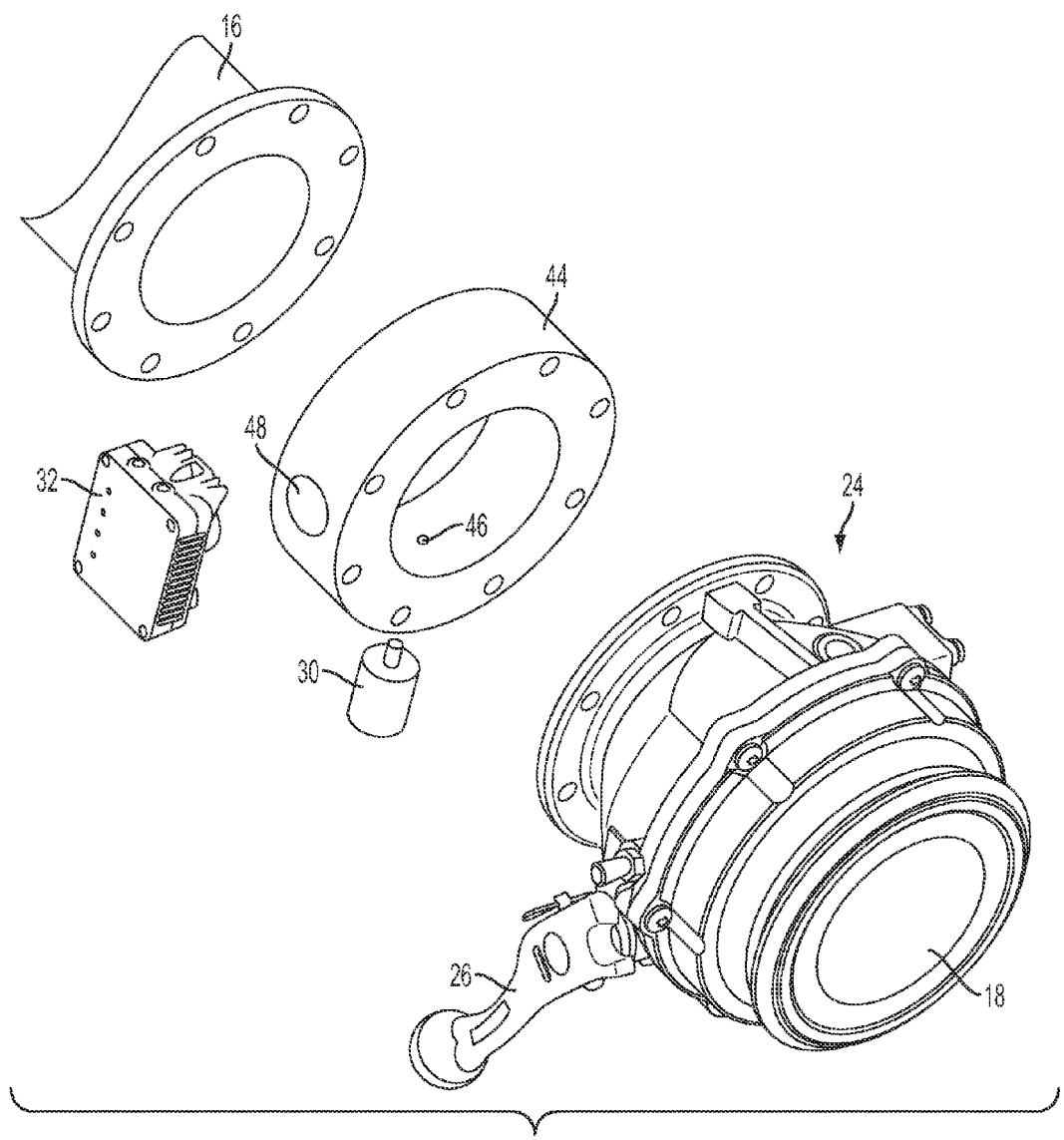
FIG. 3 is an exploded perspective view of an exemplary port for a fuel transport vehicle.

As shown in FIG. 3, the fuel level sensor 30 can be coupled to a spacer 44 that is inserted between the conduit 16 and the access valve 24. The spacer 44 can comprise an opening 46 to allow the fuel to contact the fuel level sensor 30. When the access valve 24 is closed and the emergency valve 20 is open, the fuel in the compartment 14 can statically fill the conduit 16 and the spacer 44 behind the access valve 24, allowing the fuel level sensor 30 to measure the pressure of the fuel in a static state.

As shown in FIG. 4A, an isolation valve 60 can be positioned between the fuel level sensor 30 and the spacer 44 in order to protect the fuel level sensor during times when the pressure of the fuel is exceptionally high, such as during filling of the compartment. The isolation valve 60 can be closed during a filling operation and opened during other times, such as when it is desirable to take pressure measurements. The isolation valve 60 can also isolate the fuel level sensor 30 if leaking or other failure occurs. As shown in FIG. 4A, a bleed valve 62 can be positioned opposite the fuel level sensor 30 from the isolation valve 60 to allow built up pressure to be bled off through outlet 64 as needed. The bleed valve can be closed when the fuel level sensor 30 measures pressure, and can be opened when the isolation valve is closed.

Figure 5:
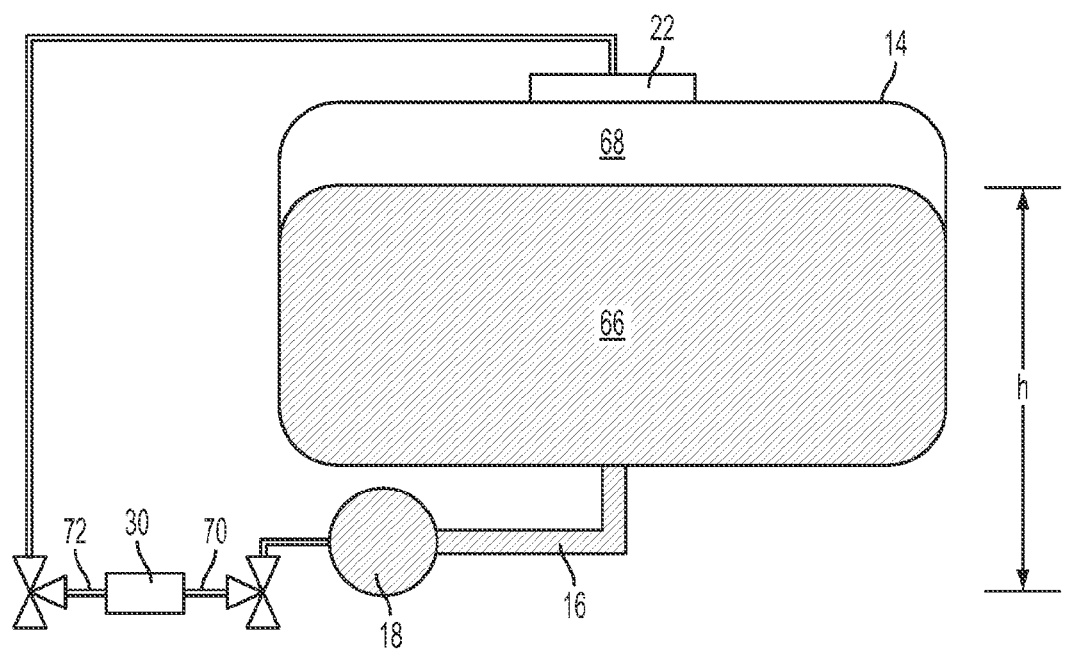
FIG. 5 illustrates an exemplary differential pressure sensor system.

As shown in FIG. 5, the fuel level sensor 30 can alternatively comprise a differential pressure sensor that compares the fluid pressure of the fuel 66 with the vapor pressure of the fuel vapor 68 built up in the top of the compartment 14. One portion 70 of the sensor 30 can measure the fluid pressure at a location adjacent to the port 18, while another portion 72 of the sensor 30 can measure the vapor pressure within the compartment 14. The second portion 72 of the sensor 30 can be fluidly coupled to the top of the compartment 14 via the hatch, for example. In this embodiment, the fuel level "h" can be proportional to the difference between the liquid pressure minus the vapor pressure, divided by the density of the fuel and the gravitational constant.

The trailer sensor(s) 36 (FIG. 2) can comprise any one or more of a variety of other types of sensors for measuring additional parameters that can be useful in monitoring the fuel. Such parameters can comprise fuel temperature, fuel vapor pressure, ambient air temperature, ambient air pressure, vehicle elevation and/or tilt, vehicle location, fuel flow rates into/out of the chambers, presence of fuel vapor outside the chambers, etc.

The fuel marker sensor 32 is configured to measure one or more characteristics of one or more fuel markers present in the fuel adjacent to the fuel marker sensor, such as the fuel flows past the fuel marker sensor, for example during unloading of the fuel through the conduit 16 and access valve 24. The marker sensor 32 can measure the concentration of the marker(s) in the fuel and/or the identity of the marker(s) in the fuel.

The fuel marker sensor 32 can be positioned along the fuel flow path between the fuel storage chamber 14 and the access valve 24. As shown in FIG. 3, in some embodiments, the fuel marker sensor 32 can be coupled to a spacer 44 positioned between the end of the conduit 16 and the access valve 24 (e.g., the fuel marker sensor 32 can be coupled to a radial opening 48 in the spacer 44, as shown in FIG. 3). In such embodiments, at least a portion of the spacer 44 can be light transparent. In some embodiments, the spacer 44 can comprise a polymeric or glass material that is clear such that fuel can be seen flowing through it during a loading or unloading operation.

By locating the fuel marker sensor 32 in-line with the fuel flow path, the sensor 32 can measure the fuel markers in real time during a loading or unloading operation. The fuel marker sensor 32 can also measure the fuel markers when the access valve 24 is closed and the fuel is static behind the access valve 24. The term "real time" means a determination of the key characteristics (e.g., the concentration of the markers, the identity of the fuel, etc.) can be performed immediately after the fuel marker sensor takes the measurements, or within a short period of time, such as less than a second, ten seconds, a minute, or some other period of time that is less than the amount of time it takes to complete the loading or unloading process. By measuring the fuel markers in real time, the relevant characteristics of the fuel and fuel markers can be available for analysis, such as by a machine or a human, before the fuel transport vehicle moves on to another location and/or performs another loading or unloading operation, which can complicate an investigation as to when the fuel may have been adulterated. In some embodiments, periodic measurements of the fuel and fuel markers can be made with the fuel marker sensor over the course of an extended period of time, such as from the time the fuel is loaded into the chamber 14 to the time it is unloaded, and stored or transmitted for later analysis.

During an unloading operation, the fuel marker sensor 32 can take several periodic measurements of the fuel marker(s) as the fuel is flowing through the spacer 44. These several measurements can provide a real time indication of the identity of the fuel that is being dispensed. The several measurements can further provide a more accurate measurement than a single measurement. In some embodiments, ten or more measurements per second can be taken by the fuel marker sensor 32.

The fuel can comprise any type of liquid fuel, such as petroleum and other hydrocarbon based fuels. Exemplary fuels can comprise diesel, oils, gasoline, natural gas, liquefied petroleum gas, biodiesel, kerosene, methane, ethane, propane, butane, pentane, hexane, octane, etc. The fuel can also comprise liquids other than petroleum based liquids, such as alcohols, hydrogen, nitrogen, and other liquids.

The fuel can comprise one or more different fuel markers. The fuel marker(s) can be specifically added to identify the particular fuel. For example, it can be predetermined that a fuel with markers A and B identifies the fuel as brand X diesel fuel and fuel with markers A and C identifies the fuel as brand Y diesel fuel. Furthermore, the concentration of the fuel markers in a fuel can be tracked to determine if the fuel has been diluted or otherwise adulterated.

The fuel markers added to the fuel are detectable by the fuel marker sensor and do not significantly interfere with the intended use of the fuel. The fuel markers can comprise a material that is miscible and/or soluble yet chemically stable in the fuel such that no chemical reaction occurs, even in the presence of water, oxygen, sunlight, varying temperature and pressures, etc. In some embodiments, the fuel markers do not significantly affect critical characteristics of the fuel, such as combustibility, viscosity, emissions, etc. In some embodiments, the fuel markers can comprise very small particles, such as nanoparticles, such as nanoparticles having an average diameter of less than one nanometer. In some embodiments, the fuel markers can comprise nanoparticles comprising phosphorus or other materials that fluoresce in response to excitation from a light source. In some examples, fuel marker concentrations can be in the range of about 1 to about 100 parts per billion (ppb), though the concentration can be greater or lower than this range depending on the particular fuel marker used.

One exemplary fuel marker is silicon 2,3-naphthalocyanine bis(trihexylsilyloxide). Synonyms comprise: 2,3-naphthalocyaninato-bis(trihexylsiloxy)silane, bis(trihexylsiloxy) silicon 2,3-naphthalocyanine. This marker has the following characteristics:

CAS number: 92396-88-8;
  Beilstein registry number: 4348502;
  Linear formula: $C_{84}H_{102}N_8O_2Si_3$;
  Molecular weight: 1340.02;
  Melting point: 270° C. (dec.) (lit.);
  UV absorption: $\lambda$max 729 nm, $\lambda$max 774 nm (2nd).

Other exemplary fuel markers can comprise fluorophores, such as from the classes of squarines, phthalocyanines, and naphthalocynannines, and other infrared fluorophores.

When excited with ultraviolet (UV) light, diesel fuel fluoresces and produces light in the blue spectrum, such as wavelengths from about 400 nm to about 600 nm. Accordingly, some fuel markers can produce light in a different spectrum relative to the fuel when it fluoresces such that the fuel marker can be differentiated by an optical detector. The relative intensity of the blue light and the non-blue light can indicate the relative concentration of the marker in the fuel. A higher intensity of non-blue light relative to the intensity of the blue light can indicate a higher concentration of the fuel marker.

Exemplary fuel markers can fluoresce in the red to near-infrared (NIR) region of the optical spectrum (e.g., wavelengths greater than about 650 nm). The fuel markers can fluoresce at higher intensity when excited by certain wavelengths of light compared to other wavelengths of light. The fuel markers can, for example, fluoresce very weakly when illuminated with UV light but strongly fluoresce when illuminated by red or NIR light.

By separately exciting and measuring the fluorescence of marked fuel with both UV light and red light, the amount of fuel present relative to the amount of marker present can be determined.

This technique of separately exciting and measuring with two different wavelength rages of light can have the benefit of being self-referencing, meaning that this technique can allow for the determination of a relative marker concentration value without the need for an external reference sample or external calibration source. This self-referencing can allow the technique to be used in in-line, live monitoring of the marked fuel as it flows out of the transport vehicle, rather that needing to take a sample to a laboratory for subsequent off-line testing.

Figure 7:
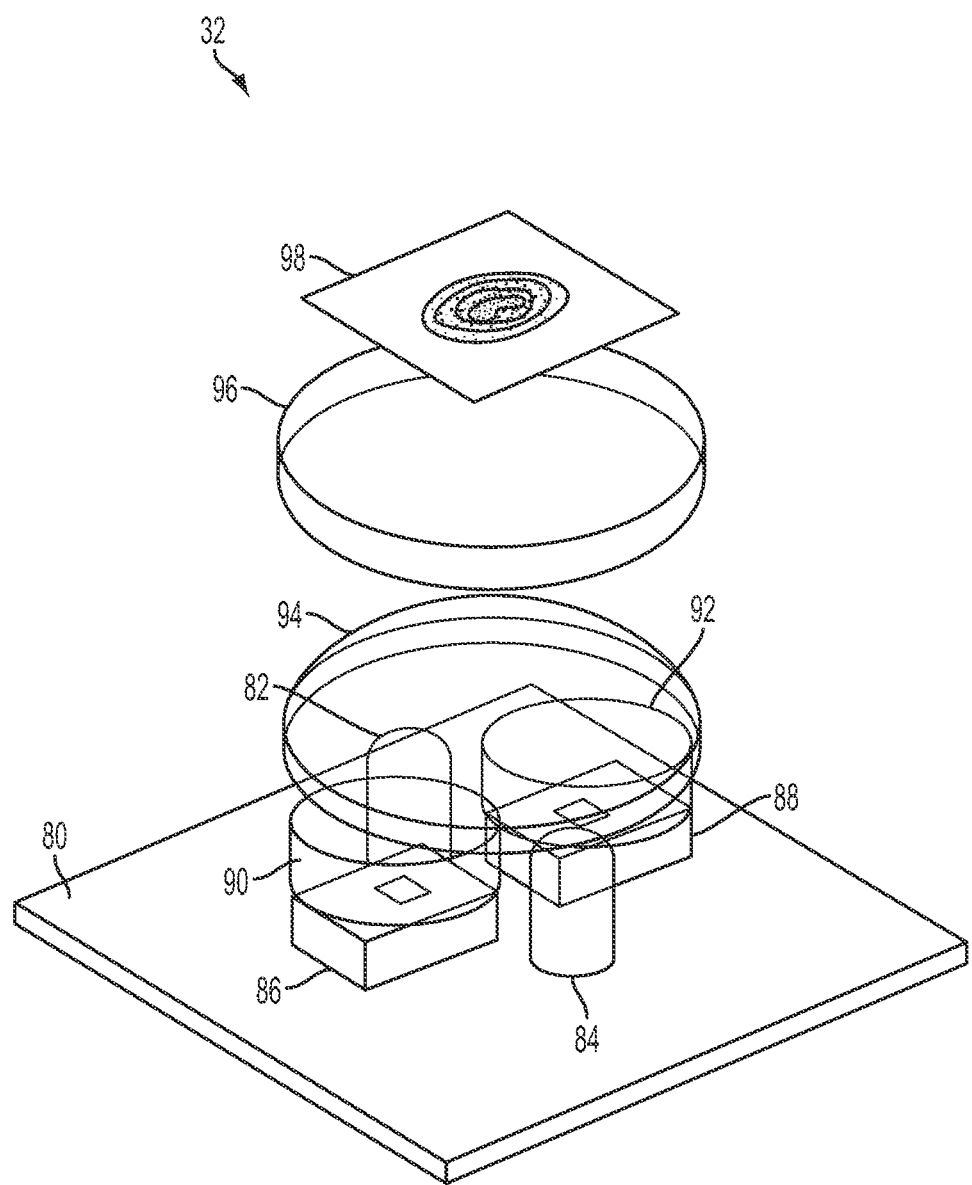
FIG. 7 is a perspective view of portions of an exemplary fuel marker sensor.
Figure 8:
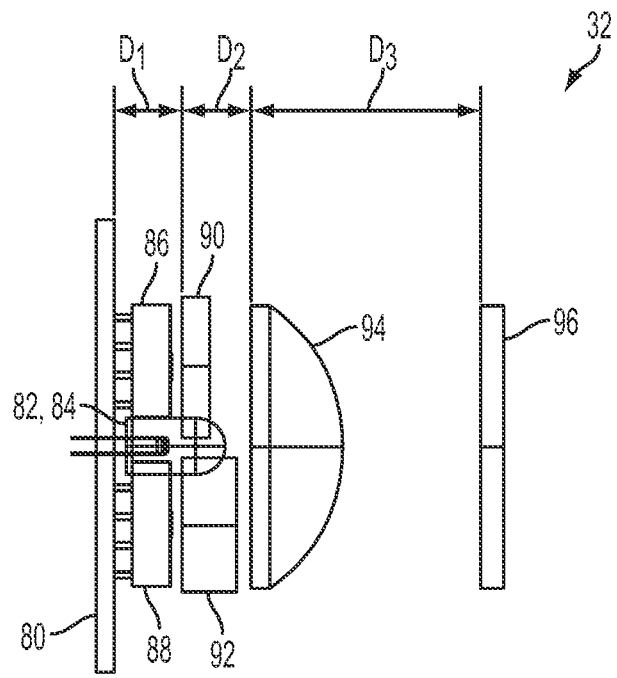
FIG. 8 is a side view of the sensor of FIG. 7.
Figure 9:
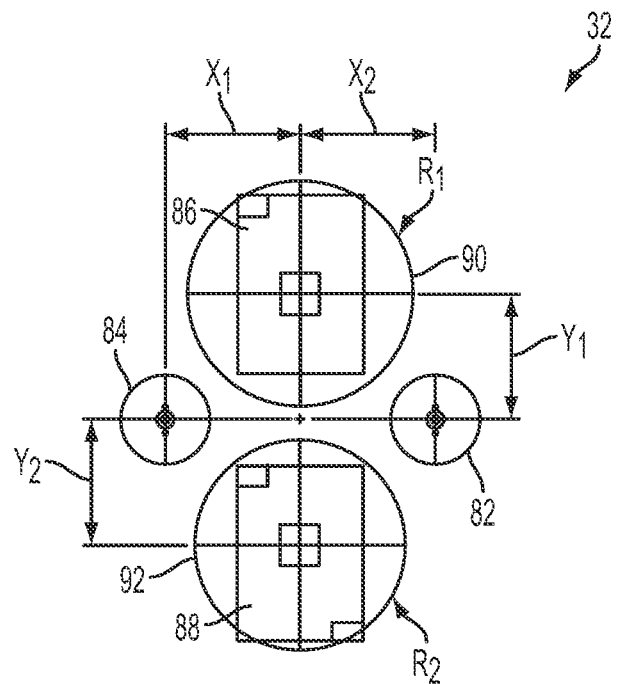
FIG. 9 is a plan view of the sensor of FIG. 7.

FIGS. 7-9 show optical components of an exemplary fuel marker sensor 32 that can be used to separately excite marked fuel with both UV light and red light and measure the fluorescence of both the fuel and the marker separately. The sensor 32 can comprise a printed circuit board 80, first and second light sources 82 and 84, first and second integrated circuit optical detectors 86 and 88, first and second filters 90 and 92, and a lens 94. The first light source, or "blue LED," 82 can be configured to emit light in the blue/UV range and can comprise a light emitting diode (LED) for example. The second light source, or "red LED," 84 can be configured to emit light in the red/NIR range can also comprise an LED. Other types of light sources can also be used to produce light in the desired wavelength ranges. The blue LED 82 produces light that is optimal for exciting the fuel itself and the red LED 84 produces light that is optimal for exciting the fuel marker. In one example, the blue LED 82 produces light with a center wavelength of about 405 nm for exciting the marker and the red LED 84 produces light with a center wavelength of about 630 nm for exciting the fuel. The two LEDs can produce light in mutually exclusive wavelength ranges.

The light from the red and blue LEDs can be directed using the lens 94 toward a region or volume of the fuel 98 that is to be measured. The region 98 is on the opposite side of the window 96, which separates the fuel from the components of the sensor 32. The region of the fuel 98 can comprise an image plane that is about one inch away from the LEDs 82, 84. The region 98 can alternatively comprise a three dimensional volume in the fuel, such as a cylindrical volume with a depth of about one inch and a diameter of about one inch.

Light from one or both of the LEDs is excites the marker and/or the fuel itself within the region 98, causing fluorescence. The fluoresced light emitted by the marked fuel is scattered, and the portion that passes back through the window 96 is directed by the lens 94 back to the light detectors 86, 88.

The first filter 90 only allows a certain range of wavelengths of the fluoresced light to reach the first light detector 86, and the second filter 92 only allows a different range of wavelengths of the fluoresced light to reach the second light detector. The first filter, or red filter, 90 can transmit light in a range corresponding the wavelength range in which the fuel marker fluoresces, such that the first light detector 86 only receives the light fluoresced from the fuel marker and not the light fluoresced from the fuel itself. Similarly, the second filter, or blue filter, 92 can transmit light in a range corresponding the wavelength range in which the fuel itself fluoresces, such that the second light detector 88 only receives the light fluoresced from the fuel itself and not the light fluoresced from the fuel marker.

Figure 6:
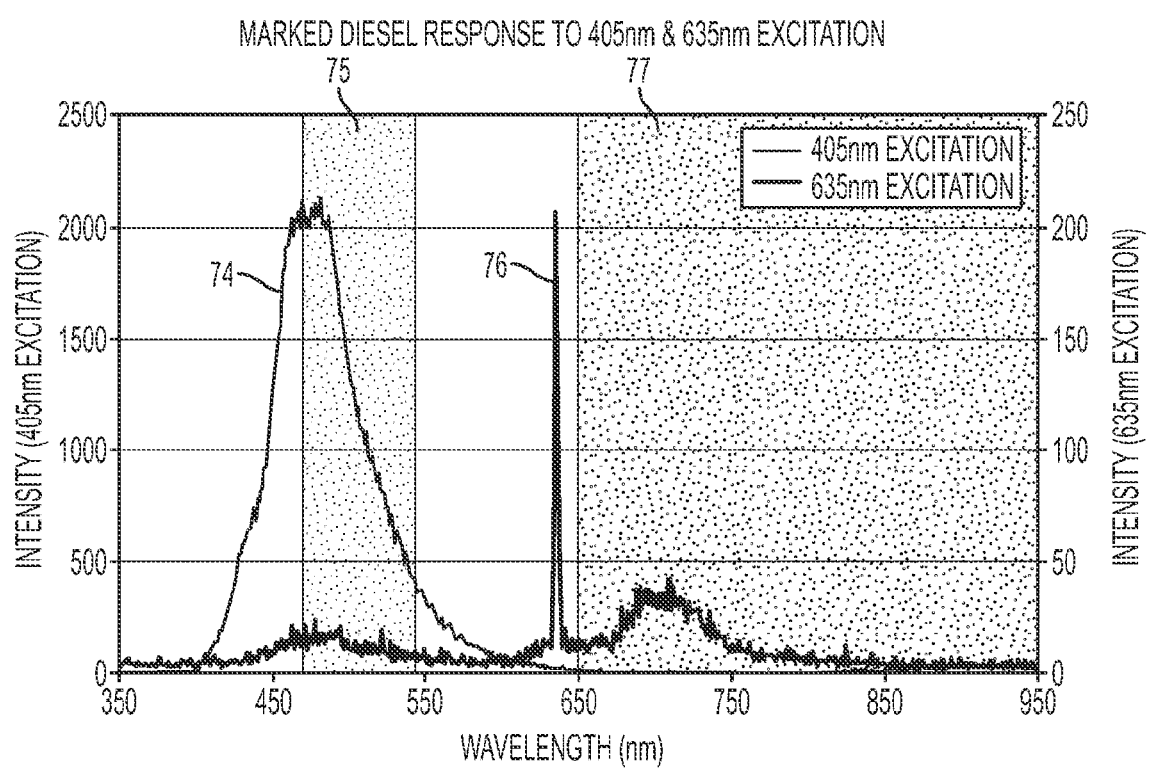
FIG. 6 is a graph of spectral response of marked diesel at two excitation wavelengths.

FIG. 6 shows an exemplary graph of the intensity of fluorescence from marked diesel as a function of wavelength in response to excitation from a blue LED centered at 405 nm and excitation from a red LED centered at 635 nm. There are two intensity measurements present in FIG. 6, the line 74 represents a response during excitation with the 405 nm light source and a filter that excludes all wavelengths shorter than 410 nm. This measurement is plotted on the left axis in FIG. 6. The line 76 is a second intensity measurement representing a response during excitation with the 635 nm source and no filter present. This measurement is plotted on the right axis in FIG. 6.

The peak of line 74 between about 450 nm and about 500 nm represents the fluorescence from the diesel fuel itself in response to the blue LED. The peak of line 76 between about 670 nm and about 740 nm represents the fluorescence from the marker in response to the red LED. As shown, the peak response from the marker is centered around 700 nm. The sharp peak in line 76 at 635 nm is the excitation illumination.

The shaded region 75 illustrates an exemplary transmissivity of the blue filter 92 and the shaded region 77 illustrates an exemplary transmissivity of the red filter 90. During the 405 nm excitation, with the blue filter 92 covering the second light detector 88, the second light detector does not sense the 405 nm excitation illumination coming from the blue LED, as all light shorter than about 470 nm is blocked by the blue filter 92. This allows only the fluorescence from the fuel between about 470 nm and about 545 nm to be detected by the second light detector 88. During the 635 nm excitation, with the red filter 90 covering the first light detector 86, the first light detector does not sense the 635 nm excitation illumination coming from the red LED, as all light shorter than about 650 nm is blocked by the red filter 90. This allows only the fluorescence from the fuel marker longer than about 650 nm to be detected by the first light detector 86.

The blue LED 82 and the red LED 84 can be turned on independently. With the blue LED 82 off and the red LED 84 on, the marker fluoresces in the red or NIR range and that light can be transmitted by the red filter 90 and detected by the first detector 86. This red fluorescence from the marker can be blocked by the blue filter 92. Similarly, with the blue LED 82 on and the red LED 84 off, the fuel itself fluoresces in the blue/UV range and that light can be transmitted by the blue filter 92 and detected by the second detector 88. This blue fluorescence from the fuel can be blocked by the red filter 90. One or more baffles (not shown) can be placed between the LEDs and the light detectors to avoid direct stimulation of the detectors from the LEDS. This can help ensure a high degree of isolation between the two measurements, which can be important for detecting small changes in marker concentration.

The fuel marker sensor 32 can cyclically switch between the red LED and the blue LED to cyclically measure the relative intensity of the marker fluorescence and the fuel fluorescence, respectively. For each cycle, the intensities of the two fluorescence events can be compared to determine the relative concentration of the marker in the fuel. If the relative concentration of the marker changes from when the fuel was loaded into the compartment 14, that can indicate that the fuel has been diluted or otherwise adulterated during that time span.

The first and second light detectors 86, 88 can be identical and/or can both detect a broad spectrum of light from UV to IR. The detectors 86, 88 can comprise integrated circuit optical detectors that comprise an integrated amplifier and are integrated with the board 80. For example, the detectors 86, 88 can comprise a silicon photodetector with an integrated, adjustable transimpedence amplifier.

The red filter 90 can comprise a 650 nm long pass filter that blocks wavelengths shorter than 650 nm but transmits wavelengths longer than 650 nm. The blue filter 92 can comprise a narrowband filter. In some embodiments the blue filter 92 can be centered on about 480 nm and can transmit wavelengths between about 470 nm and about 490 nm and block other wavelengths. In some embodiments the blue filter 92 can transmit wavelengths between about 445 nm and about 470 nm and block other wavelengths. In some embodiments, the filters 90, 92 can comprise colored glass or other suitable materials, while in other embodiments, the filters can comprise dielectric stack filters.

The lens 94 can comprises a concave side facing the LEDs and detectors and a convex side facing the region of interest 98 in the fuel. In some embodiments, a simple lens having a 30 mm focal length can be used to direct light to and from a two-dimensional image plane 98, as shown in FIG. 7. However, in some embodiments, the spherical aberration of the lens 94 can be used to spread, or defocus, the light from the LEDs over a three dimensional region within the fuel. This region can be called a "region of least confusion" and can be the optimal location for stimulating fluorescence. The lens 94 with spherical aberration can have a non-imaging optical design. The lens 94 can have varying amounts of spherical aberration, in some embodiments the spherical aberration typical of a 25.4 mm diameter, 30 mm focal length spherical plano-convcave lens is preferred.

The three dimensional region of least confusion 98 can comprise a generally cylindrical region having a central axis aligned with a center point between the two LEDs. The cylindrical region can have a depth, or height, of about one inch and a diameter of about one inch, and can be completely occupied by the fuel to be sensed. In other embodiments, the depth can be about 6 mm and the diameter can be about 5 mm.

The lens 94 can direct the light from the LEDs generally evenly about the region 98, causing fluorescence throughout the region. The scattered fluorescence entering the window 96 is then redirected by the lens 94 in a generally parallel direction toward the board 80 and detected by the detectors 86, 88.

The window 96 and/or the lens 94 can be coated with an anti-reflective coating, such as $MgF_2$, to reduce stray light reaching the detectors.

FIGS. 8 and 9 show side and plan views, respectively, of the optical components of the sensor 32. The filters 90, 92 can be spaced a distance $D_1$, which can be about 6 mm, from the board 80. The lens 94 can be spaced a distance $D_2$, which can be about 6 mm, from the bottom of the filters, or about 12 mm the board. The window 96 can be spaced a distance $D_3$, which can be about 20.2 mm, from the bottom of the lens, or about 32.2 mm from the board 80. The detectors 86, 88 can be positioned with their centers at distances $Y_1$ and $Y_2$, which can both be about 7.5 mm, from a central axis of the sensor, or about 15 mm apart from each other. The filters 90, 92 can be centered directly over the centers of the detectors 86, 88. The red filter 90 can have a radius $R_1$ of about 6.25 mm, a thickness of about 3 mm, and an 80-50 surface quality. The blue filter 92 can have a radius $R_2$ of about 5.9 mm, a thickness of about 4.8 mm, and an 80-50 surface quality. The LEDs 82, 84 can be integrally positioned on the board 80 and spaced distances $X_1$ and $X_2$, which can both be about 7.5 mm, from the center axis of the sensor 32, or about 15 mm apart from each other. The lens 94 can have a diameter that is larger than the distance between the two LEDs and the distance between the two light detectors, such as about 25 mm.

Figure 10:
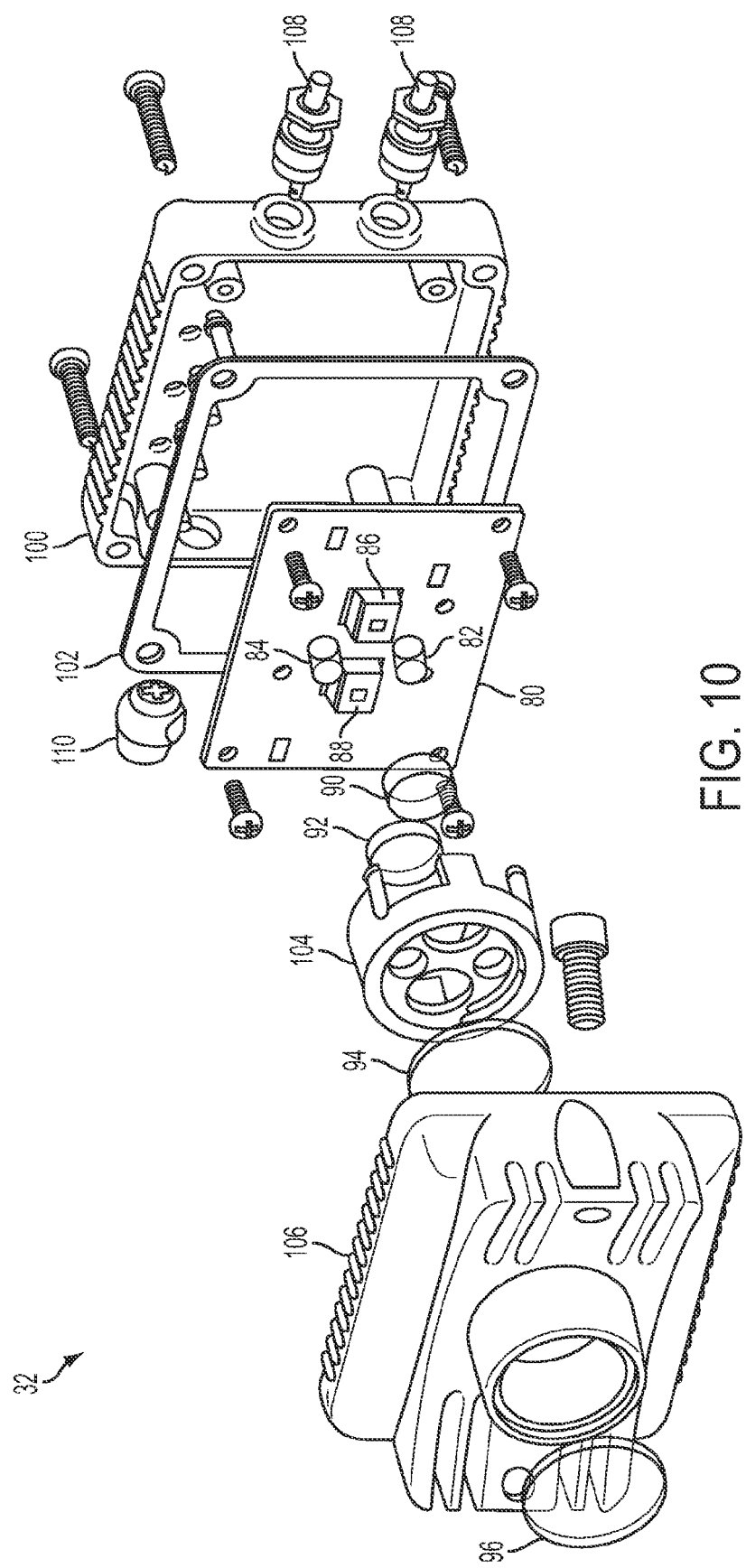
FIG. 10 is an exploded perspective view of an exemplary fuel marker sensor.
Figure 11:
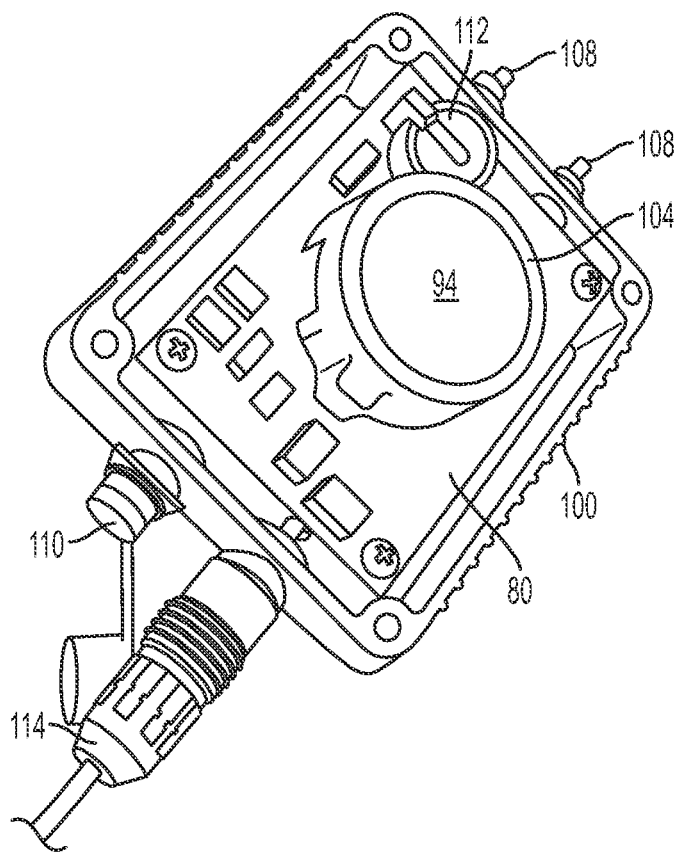
FIG. 11 is a perspective view of the sensor of FIG. 10 with a front casing removed.
Figure 12:
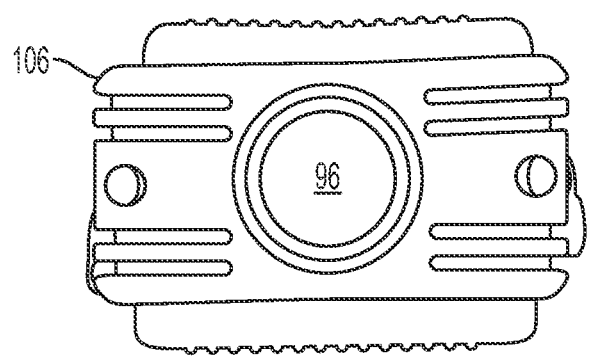
FIG. 12 is a front view of the sensor of FIG. 10.

FIGS. 10-12 show an exemplary mechanical design of the fuel marker sensor 32. The sensor 32 can comprise a rear casing 100, a gasket 102, and a front casing 106 that are sealed together, such as with screws, to form a water tight enclosure that houses the optical and electrical components of the sensor 32. The board 80 can be mounted to the rear casing 100, such as with screws. The LEDs 82, 84 and detectors 86, 88 are integrally mounted with the board 80. The filters 90, 92 and the lens 94 can be mounted in a rigid holder 104 that is attached to the board. The holder 104 can hold the filters and lens in a specific spacing and orientation relative to the LEDs and detectors. The window 96 can be mounted in an opening in the front casing 106. As shown in FIG. 11, a battery 112 can be coupled to the board 80 to provide power. One or more buttons 108 can be mounted in the side of the rear casing 100 and electrically coupled to the board 80. The buttons 108 can allow for manual control of different functions of the sensor 32. One or more electrical interface ports 110, 114 can be mounted in the rear casing 100 and electrically coupled to the board 80. The ports 110, 114 can electrically couple the sensor 32 to a controller, other components of the sensor system of the vehicle, power supplies, other sensors, computing devices, etc. The entire fuel marker sensor 32 can be about 2 to about 4 inches wide, about 1.5 to about 3 inches tall, and about 0.5 to about 1 inch thick. The front and rear casings 100, 106 can further comprise features, such as screw holes, for mounting the sensor 32 to the fuel transport vehicle. In some embodiments, the fuel marker sensor 32 can comprise an on-board temperature sensor. The board 80 can comprise a microprocessor or other similar computing device, can be reconfigurable and can provide for electronic communication with other devices.

The fuel marker sensor 32, along with other sensors of the sensor system can be electrically coupled to a controller 50 (FIG. 2). The controller can cause the fuel marker sensor 32 and/or other sensors to take measurements at certain times and can receive measurement data from the fuel marker sensor and/or other sensors. The controller 50 can perform various calculations based on the received data from the sensors, such as the determined type and/or concentration of the one or more fuel markers present in the fuel and the controller 50 can store and/or transmit the determined information. The controller 50 can be located anywhere on the fuel transport vehicle, such as on the trailer or a tractor coupled to the trailer.

In some embodiments, the sensor system can determine whether or not the liquid present in or being unloaded from a certain chamber 14 is a certain type of fuel, such as diesel. This can be a yes or no determination based on the presence or absence of one or more specific markers that identify that specific fuel.

In some embodiments, the sensor system can determine if the liquid is more than a certain percentage of a certain fuel based on the concentration of the markers. For example, the system can determine whether or not the liquid being unloaded from a chamber is greater than 99% diesel based on the concentration of a marker that was originally added to the diesel.

In some embodiments, the sensor system can determine the presence or absence of a plurality of different markers, such as eight different markers, and generate a binary code corresponding to which markers are present. For example, if marker A is present, but markers B-H are not present, the system can generate an eight-digit binary code of 1000000. Likewise, if all eight markers A-H are present, the system can generate an eight-digit binary code of 11111111. In the example of eight different markers, there can be 256 different combinations of the eight markers. Some or all of the 256 different combinations can be associated with different specific liquids. In this way, the sensor system can distinguish which fuel is present based on what combination of a given set of markers is detected in the fuel.

By identifying the fuel and determining the concentration of the fuel, the sensor system can help identify and prevent changes to the fuel between two events, such as between a loading event and an unloading event. This can in turn help identify and prevent fuel tax evasion and fraud.

The disclosed sensor systems, or any portions thereof, can be permanently or temporarily installed on an existing fuel storage vehicle. For example, a vehicle currently in use for transporting fuel can be retrofitted with a sensor system to help identify and prevent fraud related to changes to the fuel being transported. In some embodiments, for each fuel storage chamber of a transport vehicle, one or more of the disclosed sensors can be installed along with a controller. In some embodiments, the controller can be installed in a cab of the vehicle and electrically coupled to the sensors. For each fuel storage chamber, an existing sight glass positioned adjacent to the access valve can be replaced with a spacer that includes a fuel marker sensor and/or a pressure sensor coupled to it. Hatch sensors can be installed above each fuel storage chamber, and/or access valve sensors can be installed at each access valve. It is also possible to install sensors that provide information on multiple access points with a single sensor. For example, an instrumented continuous bar or rod over all the hatches, or an instrumented continuous bar or rod that would interfere with opening any of the access valves on the vehicle, could be installed to detect opening of these access points. It is also possible, in certain embodiments, to electrically monitor the condition (open or closed) of the emergency valves 20 in FIG. 1. Any of these can be installed on a vehicle without puncturing the fuel storage chambers or positioning any components within the fuel storage compartments.

By positioning the disclosed sensor systems on a fuel transport vehicle, the fuel being transported can be continuously monitored during transportation and/or during the loading and unloading processes. This can significantly improve the ability to detect and prevent fraud related to changes in the fuel compared to traditional methods where samples of the fuel need to be drawn at the time the fuel is unloaded and then taken to a laboratory and tested at a later time, after the fuel transport vehicle has unloaded and departed. With the disclosed on-board sensor systems, the identity and/or concentration of the fuel markers in the fuel can be determined in real time, such as while the fuel is being unloaded at a retail station. This information can be immediately utilized to determine if changes have occurred to the fuel and determine if fraud has occurred. In the case that fraud is detected, the unloading process can be stopped and/or the operator/owner of the vehicle can be questioned and/or otherwise held accountable before the vehicle departs. In some embodiments, the information measured and determined by the sensor system can be transmitted in real time to a remote location where other systems and/or people can analyze the information to detect fraud. This can greatly shorten the amount of time between when the fraud occurs and when it is detected.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "determine" and "provide" to describe the disclosed methods. These terms are high-level abstractions of the actual operations that are performed. The actual operations that correspond to these terms may vary depending on the particular implementation and are readily discernible by one of ordinary skill in the art.

As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled or associated items absent specific contrary language.

In view of the many possible embodiments to which the disclosed principles may be applied, it should be recognized that the illustrated embodiments are only preferred examples and should not be taken as limiting the scope of the disclosure. Rather, the scope of the disclosure is defined by the following claims. We therefore claim all that comes within the scope and spirit of these claims.

We claim:

1. A sensor system for a fuel transport vehicle, the system comprising:
    a fuel marker sensor positioned along a flow pathway between a fuel storage chamber of a fuel transport vehicle and an access valve for the fuel storage chamber, the fuel marker sensor configured to measure one or more characteristics of one or more fuel markers in fuel adjacent the fuel marker sensor.

2. The system of claim 1, wherein the one or more characteristics of the one or more fuel markers comprises a concentration of at least one of the one or more fuel markers in the fuel.

3. The system of claim 1, wherein the one or more characteristics of the one or more fuel markers comprises an identity of at least one of the one or more fuel markers in the fuel.

4. The system of claim 1, wherein the fuel marker sensor is configured to measure the one or more characteristics as the fuel flows past the fuel marker sensor.

5. The system of claim 1, wherein the fuel marker sensor is configured to measure the one or more characteristics when the access valve is closed.

6. The system of claim 1, wherein the fuel marker sensor is configured to make plural measurements per second of the one or more characteristics during a fuel dispensing event.

7. The system of claim 1, wherein at least one of the fuel markers comprises nanoparticles having an average diameter of less than one nanometer.

8. The system of claim 1, wherein the fuel marker sensor comprises at least two light sources that emit light in two respective mutually exclusive wavelength ranges and at least two light detectors that measure intensity of light received as a function of wavelength.

9. The system of claim 8, wherein the fuel marker sensor comprises a filter for each light detector, the filters transmitting light in different wavelength ranges to the respective filters.

10. The system of claim 9, wherein a first filter comprises a narrowband filter and a second filter comprises a long pass filter.

11. The system of claim 9, wherein a first filter is configured to transmit light to a first light detector in a first wavelength range corresponding to a wavelength range in which at least one of the one or more fuel markers fluoresces when excited by light from a first light source, and a second filter is configured to transmit light to a second light detector in a second wavelength range corresponding to a wavelength range in which a second fuel, similar to the fuel including the one or more fuel markers but without any fuel markers, fluoresces when excited by light from a second light source, the first and second wavelength ranges being mutually exclusive.

12. The system of claim 11, wherein the fuel marker sensor further comprises a lens having a spherical aberration configured to direct light from the first and second light sources over a three dimensional region of the fuel adjacent to the fuel marker sensor, and configured to direct light fluoresced from the fuel and the one or more fuel markers in the region of the fuel toward the first and second light detectors.

13. The system of claim 1, wherein the fuel marker sensor comprises a lens having a spherical aberration typical of a 25.4 mm diameter, 30 mm focal length spherical plano-concave lens.

14. The system of claim 1, further comprising a controller positioned on the vehicle and electrically coupled to the fuel marker sensor and configured to determine the one or more characteristics of the one or more fuel markers based on information received from the fuel marker sensor.

15. The system of claim 14, wherein the controller is configured to determine the identities of plural different markers in the fuel based on respective spectral patterns of light fluoresced by the different markers.

16. The system of claim 14, wherein the controller is configured to determine the concentration of at least one fuel marker of the one or more fuel markers based on the intensity of light fluoresced by the at least one fuel marker relative to the intensity of light fluoresced by the fuel.

17. The system of claim 14, wherein the controller is configured to determine the identity of the fuel based on the identities of the one or more fuel markers present in the fuel.

18. The system of claim 1, further comprising:
    an access valve sensor configured to detect whether the access valve is closed based on proximity of an access valve handle relative to the access valve sensor;
    a hatch sensor configured to detect whether an upper hatch of the fuel storage chamber is closed based on proximity of the hatch relative to the hatch sensor; and
    a fuel level sensor configured to measure the level of fuel within the fuel storage chamber based on fuel pressure adjacent to the access valve.

19. The system of claim 1, wherein the fuel marker sensor is attached to a light transparent annular spacer positioned between the access valve and a conduit from the fuel storage chamber to the access valve, such that the fuel marker sensor is in optical communication with fuel present within the spacer.

* * * * *

UNITED STATES PATENT AND TRADEMARK OFFICE
CERTIFICATE OF CORRECTION

PATENT NO. : 9,291,609 B2
APPLICATION NO. : 13/787430
DATED : March 22, 2016
INVENTOR(S) : Dennis Duncan Earl Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 383 days.

Signed and Sealed this
Fourteenth Day of June, 2016

Michelle K. Lee
*Director of the United States Patent and Trademark Office*